(12) United States Patent
Zhong et al.

(10) Patent No.: US 7,582,453 B2
(45) Date of Patent: Sep. 1, 2009

(54) METHOD TO CONTROL THE DISTRIBUTION OF THE STARCH SUGAR'S MOLECULAR WEIGHT IN OLIGOSACCHARIDES PRODUCTION

(75) Inventors: Zhensheng Zhong, Guangzhou (CN); Jianhua Zhu, Edmonton (CA); XiaoLin Li, Guangzhou (CN); Xiao Yan Xu, Guangzhou (CA); Xiaomei Mu, Guangzhou (CN)

(73) Assignee: Advance Will Technology Limited, Road Town, Tortola (VG)

( * ) Notice: Subject to any disclaimer, the term of this patent is extended or adjusted under 35 U.S.C. 154(b) by 521 days.

(21) Appl. No.: 11/036,181

(22) Filed: Jan. 14, 2005

(65) Prior Publication Data

US 2005/0181487 A1 Aug. 18, 2005

(30) Foreign Application Priority Data

Jan. 15, 2004 (CN) .................. 2004 1 0015132

(51) Int. Cl.
*C12P 19/04* (2006.01)
(52) U.S. Cl. ...................................... 435/101
(58) Field of Classification Search ............. 435/101
See application file for complete search history.

(56) References Cited

U.S. PATENT DOCUMENTS

| 4,081,326 A | 3/1978 | Hall |
| 4,603,110 A | 7/1986 | Morehouse et al. |
| 5,180,669 A | 1/1993 | Antrim |
| 5,652,127 A | 7/1997 | Mitchinson et al. |
| 5,736,533 A | 4/1998 | Simon et al. |
| 5,756,714 A | 5/1998 | Antrim et al. |
| 6,652,901 B2 | 11/2003 | Ishii |

FOREIGN PATENT DOCUMENTS

| CA | 1 208 586 | 7/1986 |
| CA | 2 109 368 | 1/2001 |
| CN | 1288954 | 3/2001 |
| CN | 1317492 | 10/2001 |
| EP | 0 252 730 | 1/1988 |
| WO | WO 93/09244 | 5/1993 |
| WO | WO 00/12746 | 3/2000 |

OTHER PUBLICATIONS

Wang et al. Derwent abstract for CN 1389572A (Jan. 8, 2003). Dewernt-Acc-No. 2003-363993; Derwent Week: 200335.*
Govindasamy, S., et al., "The Single Screw Extruder as a Bioreactor for Sago Starch Hydrolysis," *Food Chemistry* 60(1):1-11, 1997.
Marchal, L.M., et al., "Effect of Temperature on the Saccharide composition Obtained After α-Amylolysis of Starch," *Biotechnology and Bioengineering* 63(3):344-355, May 5, 1999.
Marchal, L.M. et al., "The Effect of Process Conditions on the α-Amylolytic Hydrolysis of Amylopectin Potato Starch: An Experimental Design Approach," *Biotechnology and Bioengineering* 62(3):348-357, Feb. 5, 1999.
Roussel, L., et al., "Sequential heat Gelatinization and Enzymatic Hydrolysis of Corn Starch in an Extrusion Reactor, Optimization for a Maximum Dextrose Equivalent," *Lebensmittel-Wissenschaft und-Technologie* 24(5):449-458, 1991.
Nakakuki, Teruo, 'Present status and future of functional oligosaccharide development in Japan', Pure Appl. Chem. vol. 74, No. 7, 1245-1251, 2002.

* cited by examiner

*Primary Examiner*—Sandra Saucier
*Assistant Examiner*—Susan Hanley
(74) *Attorney, Agent, or Firm*—Christensen O'Connor Johnson Kindress PLLC

(57) ABSTRACT

A method to control the distribution of the starch sugar's molecular weight by controlling of Ultra-low DE value during the reaction was invented. The method comprising blending starch with water to get starch slurry, and then mixing it with the 0.01%-0.03% of $CaCl_2$ based on dried starch. The next step involves adjusting the pH of the starch slurry. A further step involves adding 0.03%-0.08% of heat-resisting α-amylases based on dried starch to the starch slurry described above. A further step involves controlling the production under optimal reaction conditions.

2 Claims, No Drawings

METHOD TO CONTROL THE DISTRIBUTION OF THE STARCH SUGAR'S MOLECULAR WEIGHT IN OLIGOSACCHARIDES PRODUCTION

FIELD OF THE INVENTION

The present invention relates to a method to control the distribution of the starch sugar's molecular weight in oligosaccharides production. The distribution of the starch sugar's molecular weight is controlled by Ultra-low DE value during the enzymatic reaction.

BACKGROUND OF THE INVENTION

Starch sugars mainly containing G3 to G5 are widely applied in pharmaceutical, healthcare and food industry areas. G3 and G5 refer to the glucose units. By way of example, G3 refers to sugar that is composed of three Glucose units linked together as one component. Chinese Patent 96196047.7 introduced a method to depress the bacteria in the starch sugar compound. Starch sugars mainly containing G3 to G5 can be obtained by organic chemistry synthesis from monosaccharide and disaccharide, or by degradation of natural starch, glycolipide and glycopeptide. Other processes are also known. By way of example, Chinese patent 99117102.0 provides an enzymatic degradation process to make oligosaccharide. The oligosaccharide was obtained from the degradation of polysaccharide in plants. Chinese Patent 01109692.6 introduced a method to make oligosaccharide with Bifido Factor from root nodule.

Currently, the enzymatic hydrolysis method is the main process. It is based on starch as raw material for the industrial production of starch sugars mainly containing G3 to G5. The process is comprised of two steps. The first step is to get the maltose syrup through starch hydrolysis with α-amylases. The second step is to get the target product through transglucosylation with the co-reaction of α-amylases and α-glucosidase, and then the routine filtration, decolouration, desalting and concentration process procedures are applied to get the final product.

The processing procedure is as follows:

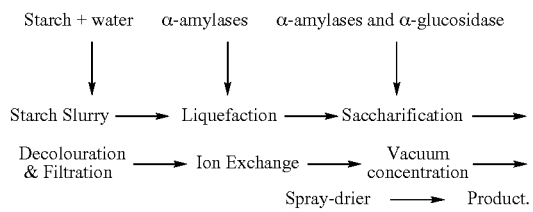

The content of G3 to G5 in the final product from the process described above is about 50% to 60%. The other main compounds are glucose and maltose which make up about 50% of the final product. The health benefits in the product are contributed by G3 to G5. A lot of glucose and maltose exist in the final product which can disturb the main two health benefits of the product. One of the main health benefits is the proliferation of beneficial microbiota bifidobacteria species in the gastrointestinal tract of humans, and the other main health benefit is the anti-dental caries function. As a result, the health benefits and commercial value of the product are significantly reduced.

SUMMARY OF THE INVENTION

What is required is a method to control the distribution of the starch sugar's molecular weight in oligosaccharides production to enhance the health benefits of the resulting product.

According to the present invention there is provided a method to control the distribution of the starch sugar's molecular weight by controlling of Ultra-low DE value during the reaction. The method comprises blending starch with water to get starch slurry, and then mixing with the 0.01%-0.03% of $CaCl_2$ based on dried starch. The next step involves adjusting the pH of the starch slurry. A further step involves adding 0.03%-0.08% of heat-resisting α-amylases based on dried starch to the starch slurry described above. A further step involves controlling the production under optimal reaction conditions.

DETAILED DESCRIPTION OF THE PREFERRED EMBODIMENT

The present invention consists of a method to control the distribution of the starch sugar's molecular weight in oligosaccharides production. The method involves blending 1 part starch with 2-4 parts water to get starch slurry, and then mixing the starch slurry with 0.01%-0.03% of $CaCl_2$ based on dried starch, and stirring to become a homogeneous mixture. A further step involves adjusting the pH of the starch slurry to 5-7. Another step involves adding 0.03%-0.08% of high temperature α-amylases based on dried starch to the starch slurry, and stirring the starch slurry to become a homogeneous mixture. Another step involves liquefying the starch slurry through a jet liquefier under the temperature of 100° C.-130° C., and controlling the DE value at 8-12. Another step involves holding the liquefied starchy liquid in a Laminar-flow tank for 20 to 60 minutes. A further step involves completing the liquefaction process and terminating the activity of enzyme once the on-line analysis of iodine-colour reaction reaches the required value. The required value can be determined by the colour of reaction of resultant in enzymatic hydrolysis of starch with iodine chemical. If the colour is blue, that means there is starch present and one must continue the enzymatic hydrolysis process. Once the colour in the on-line analysis reaches the point from blue to brown, then the activity of the enzyme must be terminated.

With the method described above, the chemical used for adjusting the pH is Na2CO3.

In the present invention, an improved and controlled Ultra-low DE technology during the jet liquefaction process is used, which combines the normal two-steps starch-liquefaction process into a one step starch-liquefaction process by suitably adjusting the amount of α-amylases. The holding time in the Laminar-flow tank is controlled within 20 to 60 minutes. Compared with the existing processes, the present invention provides the following benefits; the content of glucose in product is reduced to about 10% which is 50%-65% less than with the existing processes, and the content of G3 to G5 before purification and other further treatment is increased to 70% which is 15% higher than the with the existing processes.

The invented unique Ultra-low DE control technology can control the hydrolysis degree of starch so that the monosaccharide content from the enzymolysis of the starch can be controlled to minimal degree. The starch chain is properly hydrolyzed to polysaccharides with suitable molecular weights by controlling the amount of α-amylases during the jet liquefaction process, and then the polysaccharides are further hydrolyzed to oligosaccharides with suitable molecular weights by controlling the holding time of the enzymolysis in Laminar-flow tank. This liquefaction process can precisely control the DE value and the point to terminate the enzyme activity during the starch hydrolysis and amount of glucose from starch hydrolysis can be controlled to minimal degree.

This method is an improved innovation for the manufacturing process of G3, G4 and G5 oligosaccharides. This unique innovative technology can be made commercially available for industrial production of oligosaccharides with minimal addition of equipment to the original process procedure.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood three preferred application examples are described with reference to the accompanying process.

DESCRIPTION OF EXAMPLES

Application Example 1

Based on weight percentage (W/W), 1 part dried starch was blended with 3 parts water to get starch slurry, and then the slurry was mixed with 0.012% of $CaCl_2$ based on dried starch. The pH of the slurry was adjusted to 5.5 by $Na_2CO_3$. The 0.04 (W/W) of heat-resisting α-amylases based on dried starch was added to above starch slurry, and mixture was agitated into a homogeneous slurry. The liquefaction process was carried out through jet liquefactier under the temperature of 100° C. at DE value 9. The liquefied starch liquid was held in Laminar-flow tank for 30 minutes. The enzyme activity was terminated when the iodine-colour reaction reached the required value. The downstream process was undertaken by following the general processes of saccharification, decolouration, filtration, desalting, concentration resulting in the final product. The components in the product were as follows: Glucose 11.9%, G3 to G5 70.1%, maltose 18.0%, isomaltose 20.5%, maltotriose 4.0%, panose 25.2%, isomaltose G3 9.2%, isomaltose G4 and over G4 11.2%.

Application Example 2

Based on weight percentage (W/W), 1 part dried starch was blended with 2 parts water to get starch slurry, and then the slurry was mixed with 0.02% of $CaCl_2$ based on dried starch. The pH of the slurry was adjusted to 6 by $Na_2CO_3$. Then 0.05 (W/W) of heat-resisting α-amylases based on dried starch was added to above starch slurry, and mixture was agitated into a homogeneous slurry. The liquefaction process was carried out through jet liquefactier under the temperature of 130° C. at DE value 10. The liquefied starch liquid was held in Laminar-flow tank for 40 minutes. The enzyme activity was terminated when the iodine-colour reaction reached the required value. The downstream process was undertaken following the general processes of saccharification, decolouration, filtration, desalting, concentration resulting in the final product. The components in product were as follows: Glucose 12.2%, G3 to G5 70.9%, maltose 16.9%, isomaltose 20.8%, maltotriose 3.8%, panose 24.8%, isomaltose G3 9.6%, isomaltose G4 and over G4 11.9%.

Application Example 3

Based on weight percentage (W/W), 1 part dried starch was blended with 3 parts water to get starch slurry, and then the slurry was mixed with 0.015% of $CaCl_2$ based on dried starch. The pH of the slurry was adjusted to 6.5 by $Na_2CO_3$. Then 0.07 (W/W) of heat-resisting α-amylases based on dried starch was added to the starch slurry, and the mixture was agitated into a homogeneous slurry. The liquefaction process was carried out through jet liquefactier under the temperature of 130° C. at DE value 12. The liquefied starch liquid was held in Laminar-flow tank for 60 minutes. The enzyme activity was terminated when the iodine-colour reaction reached the required value. The downstream process followed the general processes of saccharification, decolouration, filtration, desalting, concentration resulting in the final product. The components in product were as follows: Glucose 11.4%, G3 to G5 69.4%, maltose 19.2%, isomaltose 19.7%, maltotriose 3.8%, panose 24.8%, isomaltose G3 9.6%, isomaltose G4 and over G4 11.5%.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the Claims.

The embodiments of the invention in which an exclusive property or privilege is claimed are defined as follows:

1. A method to control the distribution of the starch sugar's molecular weight in oligosaccharides production, the method comprising:
   based on weight percentage, blending 1 part dried starch with 2 to 4 parts water to get a starch slurry;
   mixing the starch slurry with 0.01%-0.03% of $CaCl_2$ (w/w) based on dried starch;
   adjusting the pH of the starch slurry to 5-7;
   based on weight percentage of dried starch, adding 0.03%-0.08% of heat resistant α-amylases to the starch slurry;
   stirring the starch slurry until it becomes a homogeneous mixture;
   liquefying the homogeneous mixture by passing the homogeneous mixture through a jet liquefier at a temperature of between 100° C. and 130° C. to form a liquefied starch liquid;
   transferring the liquid from the jet liquefier to a Laminar-flow tank;
   controlling the DE value at 8-12 while holding the liquid in the Laminar-flow tank at a temperature of between 100° C. and 130° C. for 20 to 60 minutes; and
   terminating the activity of said α-amylases once an analysis of an iodine-color reaction indicates the liquid has a glucose content of between 11.4% and 12.2% and a G3 to G5 content of 70% as indicated by a color of reaction of resultant in enzymatic hydrolysis of starch with iodine chemical.

2. The method according to claim 1, wherein the chemical used to adjust the pH is $Na_2CO_3$.

* * * * *